(12) United States Patent
Löving et al.

(10) Patent No.: US 10,159,729 B2
(45) Date of Patent: Dec. 25, 2018

(54) ANTIGEN AND METHOD FOR PRODUCTION THEREOF

(71) Applicant: Salipro Biotech AB, Södertälje (SE)

(72) Inventors: Robin Löving, Huddinge (SE); Jens Frauenfeld, Stockholm (SE); Gunilla Karlsson Hedestam, Stockholm (SE); Henrik Garoff, Hägersten (SE); Mathilda Sjöberg, Solna (SE)

(73) Assignee: Sallpro Biotech AB, Sodertalje (SE)

( * ) Notice: Subject to any disclaimer, the term of this patent is extended or adjusted under 35 U.S.C. 154(b) by 0 days.

(21) Appl. No.: 15/021,346

(22) PCT Filed: Sep. 12, 2014

(86) PCT No.: PCT/EP2014/069512
§ 371 (c)(1),
(2) Date: Mar. 11, 2016

(87) PCT Pub. No.: WO2015/036549
PCT Pub. Date: Mar. 19, 2015

(65) Prior Publication Data
US 2016/0220664 A1 Aug. 4, 2016

(30) Foreign Application Priority Data
Sep. 13, 2013 (SE) ...................... 1351057

(51) Int. Cl.
| | |
|---|---|
| *A61K 39/21* | (2006.01) |
| *A61K 39/12* | (2006.01) |
| *C12N 7/00* | (2006.01) |
| *A61K 39/00* | (2006.01) |

(52) U.S. Cl.
CPC .............. *A61K 39/21* (2013.01); *A61K 39/12* (2013.01); *C12N 7/00* (2013.01);
(Continued)

(58) Field of Classification Search
None
See application file for complete search history.

(56) References Cited

U.S. PATENT DOCUMENTS

| | | |
|---|---|---|
| 5,652,339 A | 7/1997 | Lerch |
| 7,083,958 B2 | 8/2006 | Sligar |

(Continued)

FOREIGN PATENT DOCUMENTS

| | | |
|---|---|---|
| WO | 2004073684 | 11/2004 |
| WO | 2005039534 | 9/2005 |

(Continued)

OTHER PUBLICATIONS

Winau et al. Apoptotic Vesicles Crossprime CD8 T Cells and Protect against Tuberculosis. Immunity, 2006; 24: 105-117.*
(Continued)

*Primary Examiner* — Janet L Andres
*Assistant Examiner* — Stuart W Snyder
(74) *Attorney, Agent, or Firm* — Honigman Miller Schwartz and Cohn LLP; Fernando Alberdi; Jonathan P. O'Brien

(57) ABSTRACT

The invention refers to a method for producing an antigen comprising at least one hydrophobic or partially hydrophobic antigen molecule from a virus, a bacterium, fungus, protozoan, parasite, a human neoplastic cell or an animal neoplastic, tumor or 5 cancer cell, the method comprising the steps of providing a virus, or cell comprising an antigen molecule, purifying the cell comprising the antigen molecule, solubilizing the antigen molecule in a solubilizing agent that preserves an intact antigen molecule upon solubilization and reconstituting the antigen molecule in a lipid-binding polypeptide that provides a lipid membrane mimicking environment and a reconstituted antigen particle 10 obtained by this method.

15 Claims, 5 Drawing Sheets

(52) U.S. Cl.
CPC ........... *A61K 2039/5258* (2013.01); *A61K 2039/6031* (2013.01); *A61K 2039/622* (2013.01); *C12N 2740/16034* (2013.01); *C12N 2740/16234* (2013.01)

(56) References Cited

U.S. PATENT DOCUMENTS

| | | |
|---|---|---|
| 7,575,763 B2 | 8/2009 | Sligar |
| 7,622,437 B2 | 11/2009 | Morissey |
| 7,662,410 B2 | 2/2010 | Sligar |
| 7,824,709 B2 | 2/2010 | Ryan |
| 7,691,414 B2 | 4/2010 | Sligar |
| 7,834,147 B2 | 11/2010 | Qi |
| 2002/0177551 A1 | 11/2002 | Terman |
| 2006/0057662 A1 | 3/2006 | Sligar |
| 2007/0117179 A1 | 5/2007 | Kudlicki |
| 2008/0248565 A1 | 10/2008 | Katzen |
| 2009/0269373 A1 | 1/2009 | Qi |
| 2009/0161828 A1 | 6/2009 | Katzen |
| 2009/0257950 A1 | 10/2009 | Sligar |
| 2010/0233782 A1 | 9/2010 | Katzen |
| 2010/0311595 A1 | 12/2010 | Ryan |
| 2011/0059159 A1 | 3/2011 | Sakmar |
| 2011/0104781 A1 | 5/2011 | Katzen |
| 2011/0195450 A1 | 8/2011 | Kudlicki |
| 2011/0256224 A1 | 10/2011 | Sigalov |
| 2012/0020878 A1 | 1/2012 | Qi |
| 2012/0190609 A1 | 7/2012 | Bader |
| 2016/0220664 A1 | 8/2016 | Löving et al. |

FOREIGN PATENT DOCUMENTS

| | | |
|---|---|---|
| WO | 2005081743 | 5/2006 |
| WO | 2008051818 | 12/2008 |
| WO | 2010053489 | 5/2010 |
| WO | 2012154825 | 11/2012 |

OTHER PUBLICATIONS

Munford et al. Saposin-like proteins (SAPLIP) carry out diverse functions on a common backbone structure. J. Lipid Res. 1995; 36: 1653-1663.*

Hersperger AR, Insights Into the Cytotoxic Potential of Human Cd8+ T Cells: Implications for Virologic Control of HIV, 2010, University of Pennsylvania ScholarlyCommons.*

International Search Report and Written Opinion dated Feb. 21, 2014 for related PCT Application No. PCT/EP2013/076404.

Qi et al.: "Saposin C Coupled Lipid Nanovesicles Specifically Target Arthritic Mouse Joints for Optical Imaging of Disease Severity", PLOS ONE vol. 7, No. 3, Mar. 2012, p. 33966.

Qi et al.: "Cancer-Selective Targeting and Cytotoxicity by Liposomal-Coupled Lysosomal Saposin C Protein", Clin Cancer Res, vol. 15, No. 18, 2009, pp. 5840-5851.

Ryan: "Nanobiotechnology applications of reconstituted high density lipoprotein", J Nanobiotechnology, Dec. 1, 2010; 8:28.

Rossmann et al.: "Crystal Structures of Human Saposins C and D: Implications for Lipid Recognition and Membrane Interactions", Structure 16, 809-817, May 2008.

Ryan: "Nanodisks: hydrophobic drug delivery vehicles", Expert Opin Drug Deliv. Mar. 2008; vol. 5(3), pp. 343-351.

Barral and Brenner, "CD1 antigen presentation: how it works", Nature Reviews Immunology, 7 (12):929-941, 2007.

León et al., "Saposins utilize two strategies for lipid transfer and CD1 antigen presentation", Proceedings of the National Academy of Sciences, 109(12):4357-4364, 2012.

Bruhn, "A short guided tour through functional and structural features of saposin-like proteins", Biochem. J., 389 (15):249-257, 2005.

Ciaffoni et al., "Saposin B binds and transfers phospholipids", The Journal of Lipid Research, 47 (5):1045-1053, 2006.

Popovic et al., "Structure of saposin A lipoprotein discs", PNAS, 109(8):2908-2912, 2012.

Wu et al., "Single-particle cryoelectron microscopy analysis reveals the HIV-1 spike as a tripod structure", PNAS, 107 (44):18844-18849, 2010.

Chasman, "Protein Structure-Determination, Analysis, and Applications for Drug Discovery." Table 1. 2003.

PCT International Search Report, PCT/EP2013/076404, dated Feb. 21, 2014 (4 pages).

* cited by examiner

ANTIGEN AND METHOD FOR PRODUCTION THEREOF

CROSS-REFERENCE TO RELATED APPLICATIONS

This application claims priority under 35 U.S.C. § 371 to Patent Cooperation Treaty application no. PCT/EP2014/069512, filed Sep. 12, 2014, which claims the benefit of Swedish patent application no. 13 510 57-3, filed Sep. 13, 2013, the entire contents of which are incorporated herein by reference.

TECHNICAL FIELD

The invention relates to an antigen and method for production thereof, in particular to a reconstituted antigen particle comprising at least one hydrophobic or partially hydrophobic antigen molecule from a virus, a bacterium, fungus, protozoan, parasite, a human neoplastic cell or an animal neoplastic, tumour or cancer cell, suitable for producing an antigenic composition or a vaccine for protecting against membrane enveloped viruses or bacteria, and is in particular suitable for producing an HIV vaccine such as Human Immunodeficiency Virus Type 1 (HIV-1) vaccine, but is also useful for producing vaccines or tools for producing vaccines for other membrane enveloped viruses or bacteria.

TECHNICAL BACKGROUND

The HIV-1/AIDS pandemic is the foremost infectious disease causing death and morbidity worldwide. The pandemic, which affects primarily young adults between 15 and 40 years of age, is a socio-economic as well as a burning health issue. In the countries of sub-Saharan Africa worst affected by the pandemic, the loss of young adults has impacted upon the economic output from these countries.

An effective approach to curbing the future impact of this viral disease is through the development and delivery worldwide of a safe, effective and affordable vaccine that prevents infection and transmission of the virus.

Also alternative medical treatments to a vaccine exist today. Efficient HIV-1 drugs exist today, but a downside is the immense costs associated with treatment making it less available for underprivileged third world countries and an economic burden for wealthier countries. Another downside of current treatments is the development of drug resistance. Consequently the drugs are only life prolongers and not an absolute cure. The best strategy to prevent an HIV-1 pandemic, resulting in AIDS patients, would most likely be an effective vaccine. This has been a highly prioritized research field for over 30 years but there is still no working vaccine in sight.

Typically, since a natural defense mechanism of humans and animals against viral diseases is based on a production of protective antibodies, a primary function of many vaccines against such diseases has been to elicit protective antibodies against infectious agents or parts thereof.

Since the discovery of HIV-1 in 1984, efforts to develop a prophylactic vaccine against HIV-1/AIDS infection have been intense and it is now clear that this is an unprecedented vaccine challenge. Due to the extreme genetic variability of HIV-1, a successful vaccine would need to elicit high-titer neutralizing antibodies not only against one or a few virus strains but against the enormous breadth of genetic diversity that exists among circulating viral variants, so-called broadly neutralizing antibodies (bNAbs). This is only possible if conserved and exposed viral determinants are targeted by the immune response. A further challenge with HIV-1 is that the envelope glycoprotein (Env) spikes are unstable complexes and vaccine candidates where stable spikes that preserve, or sufficiently well mimic, the native conformation of the full-length functional HIV-1 spike were so far not developed. This is likely to be a major reason for the failure of most HIV vaccine candidates developed so far.

Although the vaccine field waits for a breakthrough a lot of information has recently been gained about broadly neutralizing antibodies (bnAb). BnAb are antibodies that have been found in some HIV-1 infected persons and they are of high interest because they, binds to and, prevent most viral strains to enter target cells. These results have shown it possible for an individual's immune system to evolve a working antibody response towards HIV-1. But, still no vaccine approach has been able to generate bnAb that targets the HIV-1 virus in humans.

DESCRIPTION OF THE INVENTION

It has been realized that the targets for HIV-1 neutralizing antibodies are the exterior envelope glycoprotein, gp120, and the trans membrane glycoprotein, gp41 that are derived from proteolytic cleavage of the gp160 precursor protein in the Golgi apparatus of virus-producing cells. Trimers of non-covalently associated gp120 and gp41 form the functional spike complexes, which mediate viral entry into host target cells. Host selection pressures have made most circulating HIV-1 isolates extremely resistant to neutralizing Abs and thus only very few conserved epitopes are exposed on the functional virus spike.

These conserved targets have been subject to intense interest as templates for HIV-1 immunogenic design and include the highly conserved CD4 binding site (CD4bs) on gp120, the membrane-proximal region of gp41, a cluster of glycans on the gp120 outer domain and an epitope proximal to the base of the variable region 1 and 2 that appears to be trimer-specific. These antibody specificities were all defined by serum mapping studies of HIV-1 infected individuals possessing bNAb activity and the corresponding monoclonal antibodies (MAbs) were isolated and confirmed to mediate extremely potent and broad HIV-1 neutralization. These studies provide hope for the development of a vaccine against HIV-1 as if such Abs were induced by Env immunization they would provide a first line of defence against HIV-1 exposure and blunt the acute viremia resulting in a lower viral load "set-point". This would lead to an improved clinical prognosis for the affected individual and a reduction in transmission rate within the human population, two considerable achievements for a vaccine.

Many current vaccines against microbial pathogens comprise live attenuated or non-virulent strains of the causative microorganisms. Many vaccines comprise killed or otherwise inactivated microorganisms. Other vaccines utilize purified components of pathogen lysates, such as surface carbohydrates or recombinant pathogen-derived proteins. Vaccines that utilize live attenuated or inactivated pathogens typically yield a vigorous immune response, but their use has limitations. For example, live vaccine strains can sometimes cause infectious pathologies, especially when administered to immune-compromised recipients. Moreover, many pathogens, particularly viruses, undergo continuous rapid mutations in their genome, which allow them to escape immune responses to antigenically distinct vaccine strains.

Given the difficulty of vaccine development, many vaccines are in extremely short supply. For example, as of October 2007, there are influenza, varicella, and hepatitis A vaccine shortages in the United States. In some instances, vaccine shortages occur because not enough manufacturers devote their facilities to vaccine production to keep up with demand. In some cases, vaccine shortages are attributed to low potency of the vaccine, which means a large amount of vaccine product must be administered to each individual in order to achieve a prophylactic effect. For example, some vaccines cannot be administered as an intact organism (even if attenuated or killed) because they cause infectious pathologies. Instead, such vaccines usually comprise purified pathogen components, which typically lead to a much less potent immune response.

SUMMARY OF THE INVENTION

Thus, there is a need in the art for systems and methods for producing highly immunogenic, effective vaccines. There is also a need for improved vaccine compositions that can potently induce long-lasting immune responses. For the treatment and prevention of infectious diseases, there is a need for improved vaccine compositions that are highly immunogenic but do not cause disease.

This problem is solved by a method for producing an antigen comprising at least one hydrophobic or partially hydrophobic antigen molecule from a virus, a bacterium, fungus, protozoan, parasite, a human neoplastic cell or an animal neoplastic, tumour or cancer cell, the method comprising the steps of

- providing a virus, or cell comprising an antigen molecule,
- purifying the cell comprising the antigen molecule,
- solubilizing the antigen molecule in a solubilizing agent that preserves intact an antigen molecule upon solubilisation,
- reconstituting the antigen molecule in a lipid-binding polypeptide that provides a lipid membrane mimicking environment.

Surprisingly, it has been found that a lipid-binding polypeptide (protein), preferably a saposin-like protein, makes it possible to reconstitute a solubilized antigen from a virus, a bacterium, fungus, protozoan, parasite, a human neoplastic cell or an animal neoplastic, tumour or cancer cell. In particular the saposin-like protein acts as a lipid membrane mimicking environment that allows to produce stable antigen molecules such as membrane proteins, or membrane protein particles, having preserved structure and functionality, also at elevated temperatures of about 37° C. by means of the method according to the present invention.

Preferably the lipid-binding polypeptide is a protein of the saposin family, namely at least one of saposins A to D. Further a mixture of two or more of these particles can be used for the purposes of the invention. Particles composed of or obtained from the lipid-binding polypeptide and at least one hydrophobic or partially hydrophobic antigen molecule subsequently are referred to as lipid binding polypeptide/antigen particles.

Unexpectedly, it was found that in the presence of a lipid-binding polypeptide, preferably a saposin-like protein, a solubilized antigen self-assembles into stable lipid binding polypeptide/antigen particles without the need of a laborious upstream liposome preparation step.

The lipid-binding polypeptides used in the invention are capable of incorporating or harboring a variety of hydrophobic compounds such as lipids and membrane proteins at a physiological pH, giving rise to nanoscale complexes that are soluble and stable in an aqueous environment.

The lipid binding polypeptide preferably is a saposin-like protein (SAPLIP) or a derivative or truncated form thereof. Due to the high degree of structural and functional conservation among SAPLIPs, the features and advantages of certain embodiments of the invention with saposin A as lipid binding polypeptide are expected to also apply to other embodiments using other SAPLIPs or derivatives or truncated forms thereof as lipid binding polypeptide of the invention.

According to a preferred embodiment, the SAPLIP is saposin A, B, C or D, in particular a saposin selected from (*Homo sapiens, Equus caballus, Bos taurus, Mus musculus, Oryctolagus cuniculus, Rattus norvegicus* or *Xenopus laevis*) saposin A, saposin B, saposin C or saposin D. In one embodiment, the SAPLIP is (*Homo sapiens, Equus caballus, Bos taurus, Mus musculus, Oryctolagus cuniculus, Rattus norvegicus* or *Xenopus laevis*) saposin A, saposin B or saposin D.

Saposin C is special among the saposins in that it is capable of inducing membrane fusion, a feature which is not exhibited by the other saposins. The membrane fusion activity may not always be desirable. According to a particular embodiment of the invention the lipid binding polypeptide is a saposin-like protein (SAPLIP) or a derivative or truncated form thereof, provided that the SAPLIP is not saposin C or provided that the SAPLIP is not saposin C or a derivative or truncated form thereof.

In one embodiment, the SAPLIP is of human origin (i.e. a *Homo sapiens* SAPLIP).

In a preferred embodiment, the SAPLIP is saposin A, preferably (*Homo sapiens, Equus caballus, Bos taurus, Mus musculus, Oryctolagus cuniculus, Rattus norvegicus* or *Xenopus laevis*) saposin A, and particularly preferred human saposin A, the amino acid sequence of which is given as SEQ ID NO. 1. Saposin A is a known protein. Its expression, purification and crystallization as LDAO-detergent complex is for example, described in PNAS, Vol. 109, No. 8 (2012) 2908-2912 (Popovic et al.).

When a derivative or truncated form of saposin A is used as lipid-binding polypeptide used according to the invention, said derivative or truncated form should be amphipathic, form at least one alpha helix, and be capable of self-assembling together with solubilized antigens into lipid-binding polypeptide/antigen particles when employed in the preparation process according to the invention which is described in detail below. As used herein, the term "amphipathic" refers to polypeptides or molecules having both hydrophilic and hydrophobic regions.

Preferably, if a derivative of a SAPLIP is used, the six cysteine residues corresponding to the six cysteines in the SAPLIP founding member saposin A should be present. It is referred in this respect to the positions of the cysteines in the sequence comparison in FIGS. 4A and 4B of Bruhn (2005), Biochem J 389 (15): 249-257, which figures are hereby specifically incorporated by reference.

The lipid binding polypeptide according to the invention may also include one or more non-natural amino acids; amino acid analogs, or a peptidomimetic structure, in which the peptide bond is replaced by a structure more resistant to metabolic degradation. Hence, the product of the process of the invention and the product of the invention may be a particle that consists essentially of the lipid-binding polypeptide and a reconstituted antigen. The lipid-binding polypeptide particles/antigen particles are robust over concentrating using standard centrifugal filter units, freezing and thawing. Moreover, practical experiments revealed that these particles display a certain degree of thermostability. In addition, it is possible to freeze-dry, store and re-hydrate the particles without any major quality deterioration observable.

By means of reconstituting the antigen molecules in the lipid-binding polypeptide, the antigen molecules are solubilized into clusters of lipid binding polypeptide particles without adding any additional lipids.

Such particles can be used in immunogenic compositions, for example, as vaccine components. Antigen proteins of interest include, without limitation, gp160, wherein gp160 corresponds to gp120/gp41, of Human Immunodeficiency Virus, envelope glycoproteins of Herpes simplex virus or measles virus, the "spike" protein of the SARS virus, hemaglutinin ligand of influenza virus or parainfluenza virus. Exemplary bacterial antigens, or antigen molecules, include, but are not limited to, cell surface proteins such as the M6 protein or M proteins of *Streptococcus pyogenes*, fimbrillin of *Porphryomonas gingivalis*, InlB or ActA of *Listeria monocytogenes*, YadA of *Yersinia enterocolitica*, IcsA of *Shigella flexneri*, invasin of *Yersinia pseudotuberculosis*, products of the acf gene of *Vibrio cholerae*, capsular material comprising the poly-D-glutamate polypeptide of *Bacillus anthracis*, fibrinogen/fibrin binding protein of *Staphylococcus aureus*, V and/or W antigens of *Yersinia pestis* (especially from a vaccine strain such as EV76) or from *Yersinia enterocolytica* or *Yersinia pseudotuberculosis*, and flagellin or porin of *Campylobacter jejuni*. Similarly, O antigens of *Salmonella typhi, Salmonella choleraesuis*, and *Salmonella enteritidis* can be combined with lipid-binding polypeptides to form lipid-binding polypeptides/antigen particles, using the proteins and methods described herein.

One aspect of the invention is the provision of vaccines. A vaccine according to the invention typically contains an antigen. In one embodiment of the invention, the antigen is physically 'bound' to the lipid-binding polypeptide by covalent or non-covalent means. Non-covalently bound includes, for example, ionic bonding, hydrophobic bonding, physical entrapment, and the like, all described in greater detail below. Such nano-carriers which themselves carry an antigen are included in the category referred to below as vaccine nano-carriers. In another embodiment, the nano-carrier has bound to it an immunostimulatory agent for enhancing, suppressing, directing, or redirecting an immune response, preferably to an antigen. In this case, the antigen may be mixed with the preparation of agent bound nano-carrier to which the immunostimulatory agent is bound form the vaccine. The antigen, of course may also be bound to a nano-carrier, including as discussed below, the same nano-carrier to which the immunostimulatory agent is bound.

According to another aspect, the present invention further provides immunogenic compositions comprising lipid binding polypeptide/antigen particles with at least one hydrophobic or partially hydrophobic antigen molecule being incorporated in the particles, preferably together with a pharmaceutically acceptable carrier. Optionally an adjuvant and/or an immune stimulant, such as a chemokine, can be incorporated into the composition. The particles allow the stabilization and solubilisation of a hydrophobic antigen, with the maintenance of the native conformation of the antigen, and with the presentation of hydrophilic regions of the antigen exposed to the aqueous environment, according to our best understanding leading to an improved immune response in the human or animal to which the immunogenic composition has been administered.

Antigens which are hydrophobic or partially hydrophobic can be formulated into immunogenic compositions for administration to a human or animal in which an immune response, either cellular or humoral, are desired. The incorporation of the antigen into the lipid-binding polypeptide/antigen particles with the method according to the invention allows the preparation of stable aqueous preparations which do not have a tendency to aggregate. Incorporation does not mean that the antigen is fully surrounded by the lipid-binding polypeptide. At least one antigenic determinant of the antigen is presented to the aqueous phase, with the more hydrophobic portions of the antigen being buried within the hydrophobic central region of the lipid binding polypeptide/antigen particle. The antigen incorporated within the particles can be a protein, such as a cell membrane protein or another antigen such as a viral envelope protein, or it can be a lipopolysaccharide or a lipooligosaccharide.

The antigen can be derived from a particle or cell, such as a virus, for instance an enveloped virus, a bacterium including, but not limited to, a bacterium, fungus, protozoan, parasite, or it can be derived from a particular type of tumour or cancer. The antigen-containing particle composition can be administered in prophylactic or therapeutic treatment regimens to generate an immune response, and administration of these particles can be carried out in combination with other vaccine preparations for priming and/or boosting.

Cancers (neoplastic conditions) from which cells can be obtained for use as an antigen source in the methods of the present invention include carcinomas, sarcomas, leukemias and cancers derived from cells of the nervous system. These include, but are not limited to bone cancers (osteosarcoma), brain cancers, pancreatic cancers, lung cancers such as small and large cell adenocarcinomas, rhabdosarcoma, mesiothelioma, squamous cell carcinoma, basal cell carcinoma, malignant melanoma, other skin cancers, bronchoalveolar carcinoma, colon cancers, other gastrointestinal cancers, renal cancers, liver cancers, breast cancers, cancers of the uterus, ovaries or cervix, prostate cancers, lymphomas, myelomas, bladder cancers, cancers of the reticuloendothelial system (RES) such as B or T cell lymphomas, melanoma, and soft tissue cancers.

The terms "neoplastic cell", "tumour cell", or "cancer cell", used either in the singular or plural form, refer to cells that have undergone a malignant transformation that makes them harmful to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumour, a "clinically detectable" tumour is one that is detectable on the basis of tumour mass; e.g., by such procedures as CAT scan, magnetic resonance imaging (MRI), X-ray, ultrasound, or palpation. Biochemical or immunologic findings alone may be insufficient to meet this definition.

Pathogens to which multiple antigen immunological responses are advantageous include viral, bacterial, fungal and protozoan pathogens. Viruses to which immunity is desirable include, but are not limited to, hemorrhagic fever viruses (such as Ebola virus), immune deficiency viruses (such as feline or human immunodeficiency viruses), herpes viruses, coronaviruses, adenoviruses, poxviruses, picornaviruses, orthomyxoviruses, paramyxoviruses, rubella, toga viruses, flaviviruses, bunyaviruses, reoviruses, oncogenic viruses such as retroviruses, pathogenic alphaviruses (such as Chikungunya virus), rhinoviruses, hepatitis viruses (e.g. Group B, C), influenza viruses, among others. Bacterial pathogens to which immune responses are helpful include, without limitation, staphylococci, streptococci, pneumococci, salmonellae, escherichiae, yersiniae, enterococci, clostridia, corynebacteria, hemophilus, neisseriae, bacteroides, francisella, legionella, pasteurellae, brucellae, mycobacteriae, bordetella, spirochetes, actinomycetes, chlamydiae, mycoplasmas, rickettsias, and others. Pathogenic fungi of interest include but are not limited to *Candida*, cryptococci, blastomyces, histoplasma, coccidioides, phycomycetes, trichodermas, aspergilli, pneumocystis, and others. Protozoans to which immunity is useful include, without limitation, toxoplasma, plasmodia, schistosomes, amoebae, giardia, babesia, leishmania, and others. Other parasites include the roundworms, hookworms and tapeworms, filiaria and others.

A further aspect of the invention is the administration of the antigen-containing immunogenic particle compositions of the invention to a human or animal (e.g. horse, pig, cow, goat, rabbit, mouse, hamster) to generate immune responses, such as production of antibody specific to the antigen or a cellular response such that cells or tissues sharing the antigen are the subject of a cellular or cytotoxic immune response. Sera or cells collected from such humans or animals are useful in providing polyclonal sera or cells for the production of hybridomas that generate monoclonal sera, such antibody preparations being useful in research, diagnostic, and therapeutic applications.

While the generation of an immune response includes at least some level of protective immunity directed to the tumour cell (or neoplastic condition), pathogen or parasite, the clinical outcome in the patient suffering from such a neoplastic condition or infection with a parasite or a pathogen can be improved by also treating the patient with a suitable chemotherapeutic agent, as known to the art. Where the pathogen is viral, an anti-viral compound such as acyclovir can be administered concomitantly with the lipid binding polypeptide/antigen particle vaccination in patients with herpes virus infection, or HAART (highly active antiretroviral therapy) in individuals infected with HIV. Where the pathogen is a bacterial pathogen, an antibiotic to which that bacterium is susceptible is desirably administered and where the pathogen is a fungus, a suitable antifungal antibiotic is desirably administered.

Similarly, chemical agents for the control and/or eradication of parasitic infections are known and are advantageously administered to the human or animal patients using dosages and schedules well known to the art. Where the patient is suffering from a neoplastic condition, for example, a cancer, the administration of the immunogenic composition comprising the lipid binding polypeptide/antigen particles carrying one or more multiplicity of cancer-associated antigens in the patient to which it has been administered is desirably accompanied by administration of antineoplastic agent(s), including, but not limited to, such chemotherapeutic agents as daunorubicin, taxol, thioureas, cancer-specific antibodies linked with therapeutic radionuclides, with the proviso that the agent(s) do not ablate the ability of the patient to generate an immune response to the administered lipid binding polypeptide/antigen particles and the antigens whose expression they direct in the patient. Nucleic acids for modulating gene expression or for directing expression of a functional protein can be incorporated within the particles, especially where the nucleic acid molecules form complexes with cationic lipids, many of which are commercially available.

The virus or cell comprising the antigen molecule can be provided for instance as a virus, or virus-like particle. The solubilizing agent for solubilizing a structure comprising the antigen molecule can be a solvent such as HEGA-10, HEGA-11, MEGA-10, Cymal-5, or any other known solubilizing agent that has been proven to preserve an intact antigen molecule such as a membrane protein upon solubilisation.

In addition to the hydrophobic membrane component, that serves as antigen, further lipid components can be used for the preparation of the lipid-binding polypeptide/antigen particles. They can be selected from naturally occurring lipids, synthetic lipids, modified lipids, fats, waxes, sterols, fat-soluble vitamins, monoglycerides, diglycerides, triglycerides, phospholipids, fatty acids, glycerolipids, glycerophospholipids, sphingolipids, saccharolipids, polyketides, sterol lipids and prenol lipids or combinations thereof.

Pharmaceutical formulations, such as vaccines or other immunogenic compositions, of the present invention comprise an immunogenic amount of the antigen-bearing particles in combination with a pharmaceutically acceptable carrier. An "immunogenic amount" is an amount of the antigen-bearing particles which is sufficient to evoke an immune response in the subject to which the pharmaceutical formulation is administered. Depending on the setting for administration (i.e., disease treatment or prevention), the dose (and repetition of administration) can be chosen to be therapeutically effective or prophylactically effective.

Exemplary pharmaceutically acceptable carriers include, but are not limited to, sterile pyrogen-free water and sterile pyrogen-free physiological saline solution. Subjects which may be administered immunogenic amounts of the antigen-carrying particles of the invention include, but are not limited to, human and animal (e.g., dog, cat, horse, pig, cow, goat, rabbit, donkey, mouse, hamster, monkey) subjects. Immunologically active compounds such as cytokines and/or BCG can also be added to increase the immune response to the administered immunogenic preparation.

Immunogenic compositions comprising the lipid binding polypeptide/antigen particles which incorporate antigens of interest produced using the methods of the invention may be formulated by any of the means known in the art. Such compositions, especially vaccines, are typically prepared as injectables, either as liquid solutions or suspensions. Solid forms suitable for solution in, or suspension in, liquid prior to injection may also be prepared. The active immunogenic ingredients are advantageously mixed with excipients or carriers that are pharmaceutically acceptable and compatible with the active ingredient. Suitable excipients include but are not limited to sterile water, saline, dextrose, glycerol, ethanol, or the like and combinations thereof.

In addition, if desired, the immunogenic compositions, including vaccines, may contain minor amounts of auxiliary substances such as wetting or emulsifying agents, pH buffering agents, and/or adjuvants which enhance the effectiveness of the vaccine. Examples of adjuvants which may be effective include but are not limited to aluminium hydroxide; N-acetyl-muramyl-L-threonyl-D-isoglutamine (thr-MDP); N-acetyl-nor-muramyl-L-alanyl-D-isoglutamine (CGP 11637, referred to as nor-MDP); N-acetylmuramyl-L-alanyl-D-isoglutaminyl-L-alanine-2-(1'-2'-dipalmitoyl-sn-glycero-3hydroxyphosphoryloxy)-ethylamine (CGP 19835A, referred to as MTP-PE); and RIBI, which contains three components extracted from bacteria, monophosphoryl lipid A, trehalose dimycolate and cell wall skeleton (MPL+TDM+CWS) in a 2% squalene/Tween 80 emulsion. The effectiveness of an adjuvant may be determined by measuring the amount of antibodies directed against the immunogenic component of the nanoscale particles after administration. Such additional formulations and modes of administration as known in the art may also be used.

The immunogenic (or otherwise biologically active) antigen-containing particle compositions can be administered in a manner compatible with the dosage formulation, and in such amount as will be prophylactically and/or therapeutically effective. Precise amounts of the active ingredient required to be administered may depend on the judgment of the physician, veterinarian or other health practitioner and may be peculiar to each individual, but such a determination is within the skill of such a practitioner.

The vaccine or other immunogenic composition may be given in a single dose or multiple dose schedules. A multiple dose schedule is one in which a primary course of vaccination may include 1 to 10 or more separate doses, followed by other doses administered at subsequent time intervals as required to maintain and or reinforce the immune response, e.g., at weekly, monthly or 1 to 4 months for a second dose, and if needed, a subsequent dose(s) after several months or years. Hydrophobic or partially hydrophobic antigens can be incorporated into the particles as described for other molecules, such as membrane proteins or small molecules. Where the antigen is in nature associated with or is within a membrane, either a solubilized pure or partially pure preparation or a solubilized membrane or membrane fragment preparation can be used as the source of the input antigen in the particle assembly mixture.

According to an embodiment of the invention, the antigen molecule is reconstituted in a lipid-binding polypeptide that comprises an amphipathic α-helical peptide having a hydrophobic or neutral face and a hydrophilic face.

According to an embodiment of the invention an antigen molecule comprising an integral membrane protein is solubilized and reconstituted.

Herein this disclosure, the term "integral protein particle" includes any of an integral membrane protein, integral membrane protein complex, a peripheral membrane protein and peripheral membrane protein complex without any limitation.

According to an embodiment of the invention, the reconstituted integral membrane protein particle is an HIV spike protein.

In this way, a dynamical and flexible HIV spike protein can be correctly presented to an individual's immune system during vaccination, which has not been presented until now according to our best knowledge despite the extensive research efforts being made under a long period of time.

The uncomplicated method according to the invention is suitable for industrial large scale production of reconstituted membrane proteins suitable for vaccine production or tools for vaccine production, in particular for vaccine production of vaccines against viral fusion proteins of type 1, type 2, type 3, such as HIV vaccines, in particular HIV-1 vaccines. But, the method according to the invention is also suitable for other membrane enveloped viruses than viral fusion proteins including other integral membrane proteins, than the above HIV spike protein, such as other integral membrane protein complexes from bacteria.

Alternatively, the method according to the invention may also be applied to integral membrane proteins from eukaryote cells or other peripheral membrane proteins.

Herein, the term "peripheral membrane protein" is referred to protein or protein complexes that are only temporarily associated to lipid membranes. Typically, peripheral membrane proteins exist in viruses, bacteria and eukaryotes.

According to an embodiment of the invention, there is provided an immunogenic composition comprising lipid-binding polypeptide/antigen particles comprising at least one hydrophobic or partially hydrophobic antigen molecule from a virus, a bacterium, fungus, protozoan, parasite, a human neoplastic cell or an animal neoplastic, tumour or cancer cell, wherein said immunogenic composition optionally further comprises a known immunological adjuvant.

According to another embodiment of the invention there is provided a reconstituted antigen particle comprising at least one hydrophobic or partially hydrophobic antigen molecule from a virus, a bacterium, fungus, protozoan, parasite, a human neoplastic cell or an animal neoplastic, tumour or cancer cell, reconstituted in a lipid membrane mimicking environment selected from a lipid-binding polypeptide such that the antigen molecules(s) is/are assembled therein.

Preferably the lipid-binding polypeptide is a saposin-like protein. According to a further preferred embodiment the saposin-like protein is selected from one or more of Saposin A, B, C and D. Particularly preferred is saposin A.

According to yet another aspect of the invention there is provided a use of an antigen, such as a reconstituted membrane protein as a tool for vaccine production, for instance a tool to find and characterize proper HIV immune response, i.e. use them as diagnostic tools to measure the proper antibody response in HIV infected patients or follow the same response for vaccinated experimental animals or vaccinated patients.

According to another aspect of the invention, there is provided a prophylactic or therapeutic use of an immunogenic composition, comprising the lipid binding polypeptide/antigen particle described herein.

BRIEF DESCRIPTION OF DRAWING FIGURES

To further explain the invention, embodiments and examples thereof the invention will now be described in greater detail with reference to the drawings.

Figure 3:
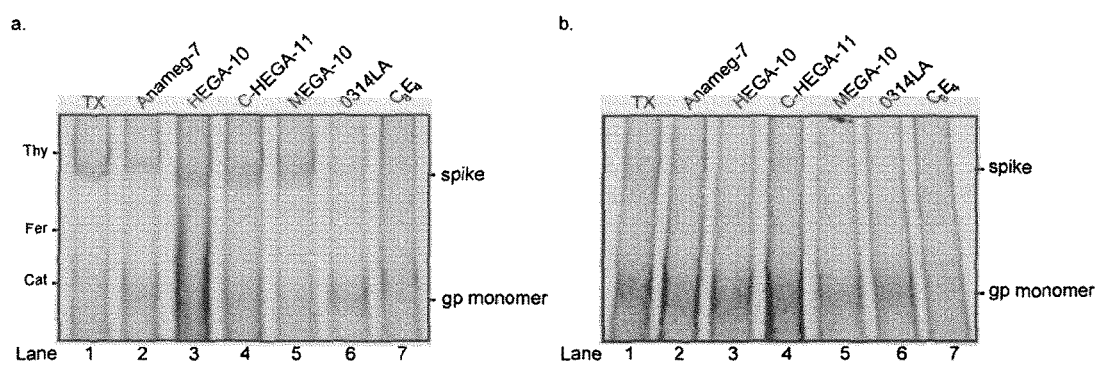

FIG. 3 schematically illustrates the solubilisation of radioactively labelled HIV-1 VLP with high CMC detergents.

Figure 4:
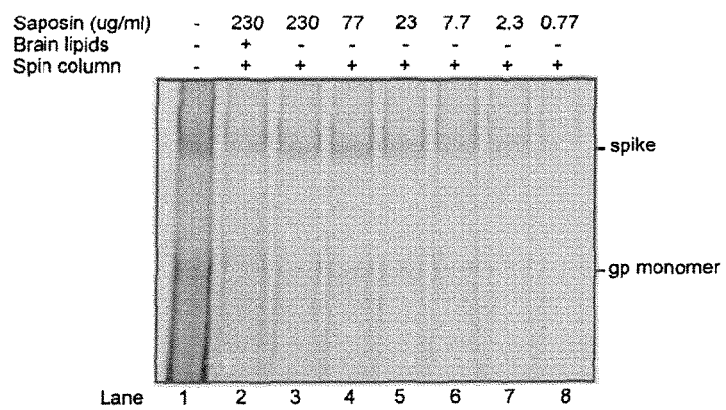

FIG. 4 shows the optimisation of the amount of Saposin A needed for efficient Salipro-HIV-spike nanoparticle formation.

Figure 5:
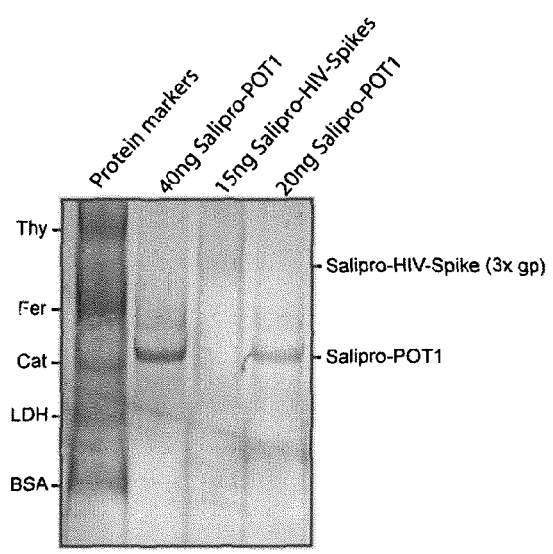
Figure 6:
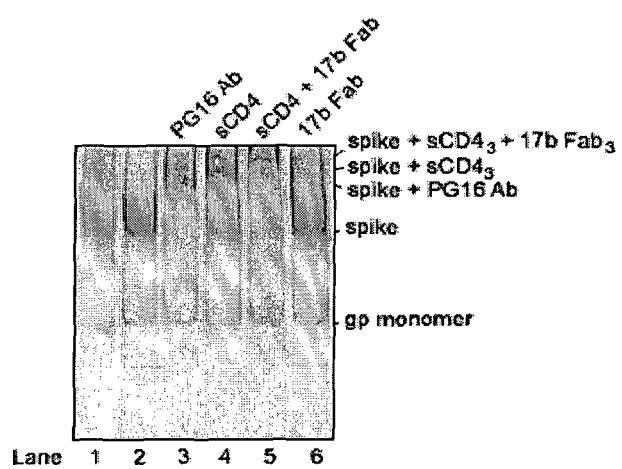
Figure 7:
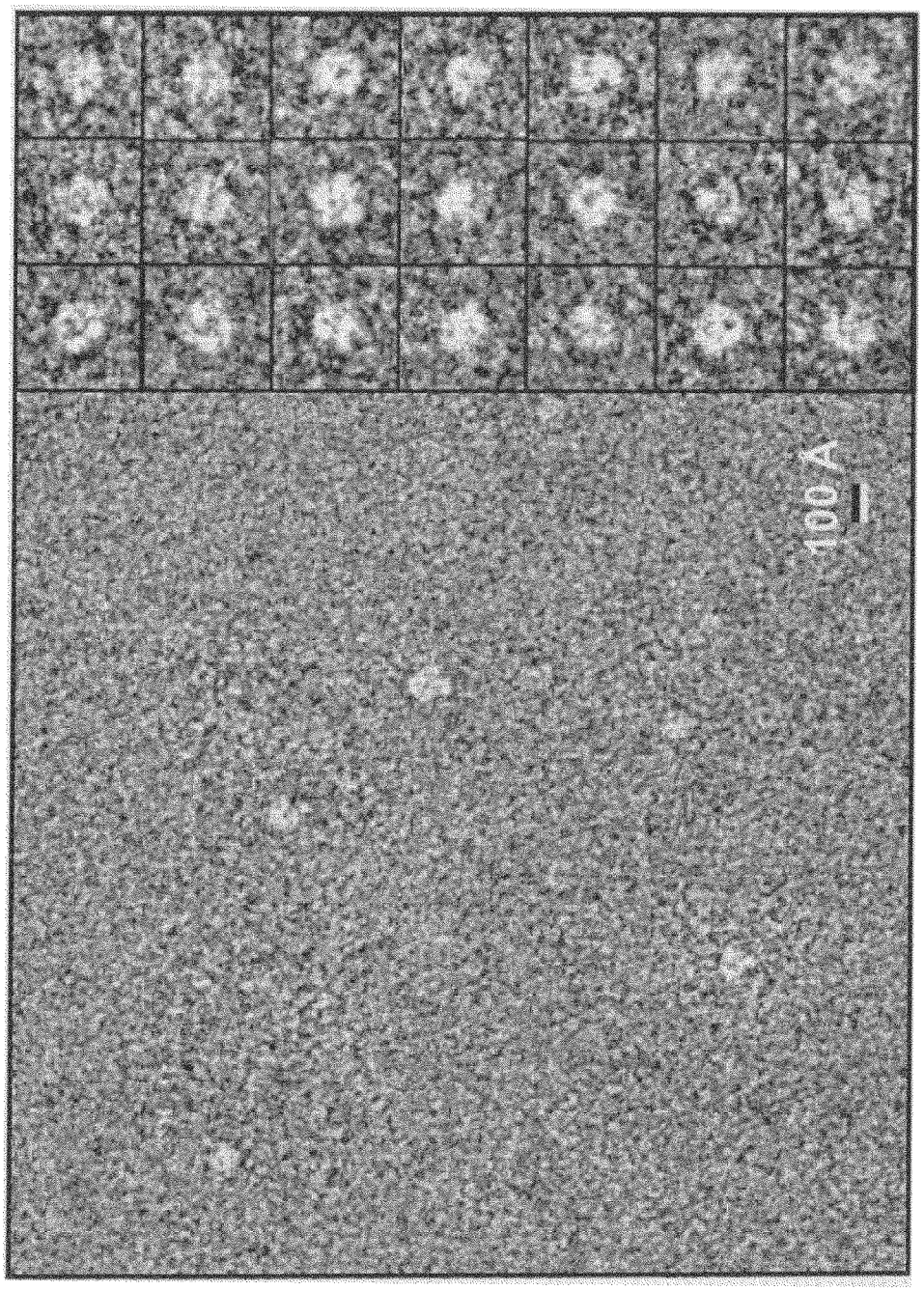

FIG. 5 shows BN-PAGE and silver stain analyses of Saposin A-POT1 and purified Saposin A-HIV-spike particles;

FIG. 6 illustrates stability, preserved structure and functionality of HIV-1 spike in Saposin A nanoparticles;

FIG. 7 illustrates negative stain EM analysis of purified Saposin A-HIV-spike particles.

Figure 1:
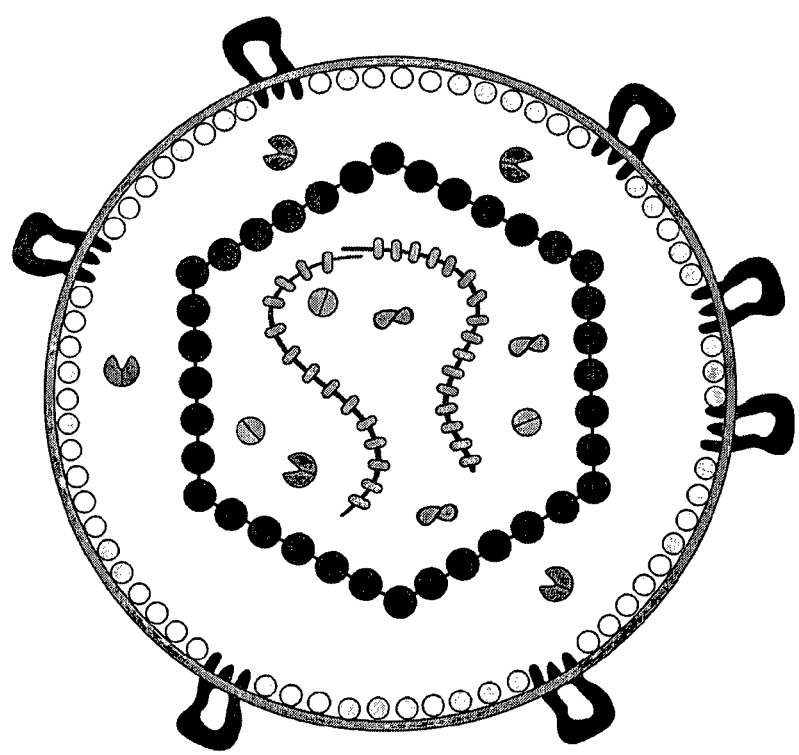
FIG. 1 is a schematic illustration of a retrovirus such as a HIV-1 virus.

FIG. 1 is a schematic illustration of a retrovirus particle. The virion is a spherical particle surrounded by a phospholipid bilayer which harbours the viral spike proteins. A HIV-1 virus particle typically comprises a viral lipid membrane enveloping a matrix layer, which envelopes viral RNA, Capsid, Integrase and Reverse Transcriptase. The lipid membrane is integrated with HIV spike proteins being anchored at multiple positions. The HIV spike protein can be considered to be an integrated membrane protein. In HIV virus particles, the proteins expressed in the viral lipid membrane are called "Envelope glycoproteins" (Env). Env contains two subunits that are non-covalent connected, referred to as gp120-gp41. The HIV spike protein is an oligomer, being a trimer of a gp120/gp41 subunit pair of a docketing glycoprotein/trans-membrane glycoprotein complex, anchored in the viral lipid membrane 2 and needed for the virus to enter target cells (not illustrated). Thus, the trimers of gp120/gp41-sub-unitpairs can be considered to form the spike proteins (Adapted from Retroviruses, Cold Spring Harbour Press, J. M. Coffin, S. H. Hughes and H. E. Varmous, 1995).

It has been realized that isolated bnAb targets the spike proteins and consequently a working vaccine should contain this protein complex. Further it has been realized that a complete functional spike protein as it appears in the virus membrane would constitute an ideal antigen, since the spike proteins are the only proteins on intact HIV-1 particles. Thus, an immune response against the spike proteins is important to stop virus particles to enter host cells. This differs from and is an advantage to other vaccine strategies which use HIV proteins, but will not prevent virus particles to spread. A problem is that spike proteins are unstable complexes and it's not known until how to preserve a functional spike protein, which is considered to be essential for being able to produce a functional vaccine against HIV. It has been realized that even HIV (virus) particles may contain incomplete assembled or disassembles spike proteins.

Figure 2:
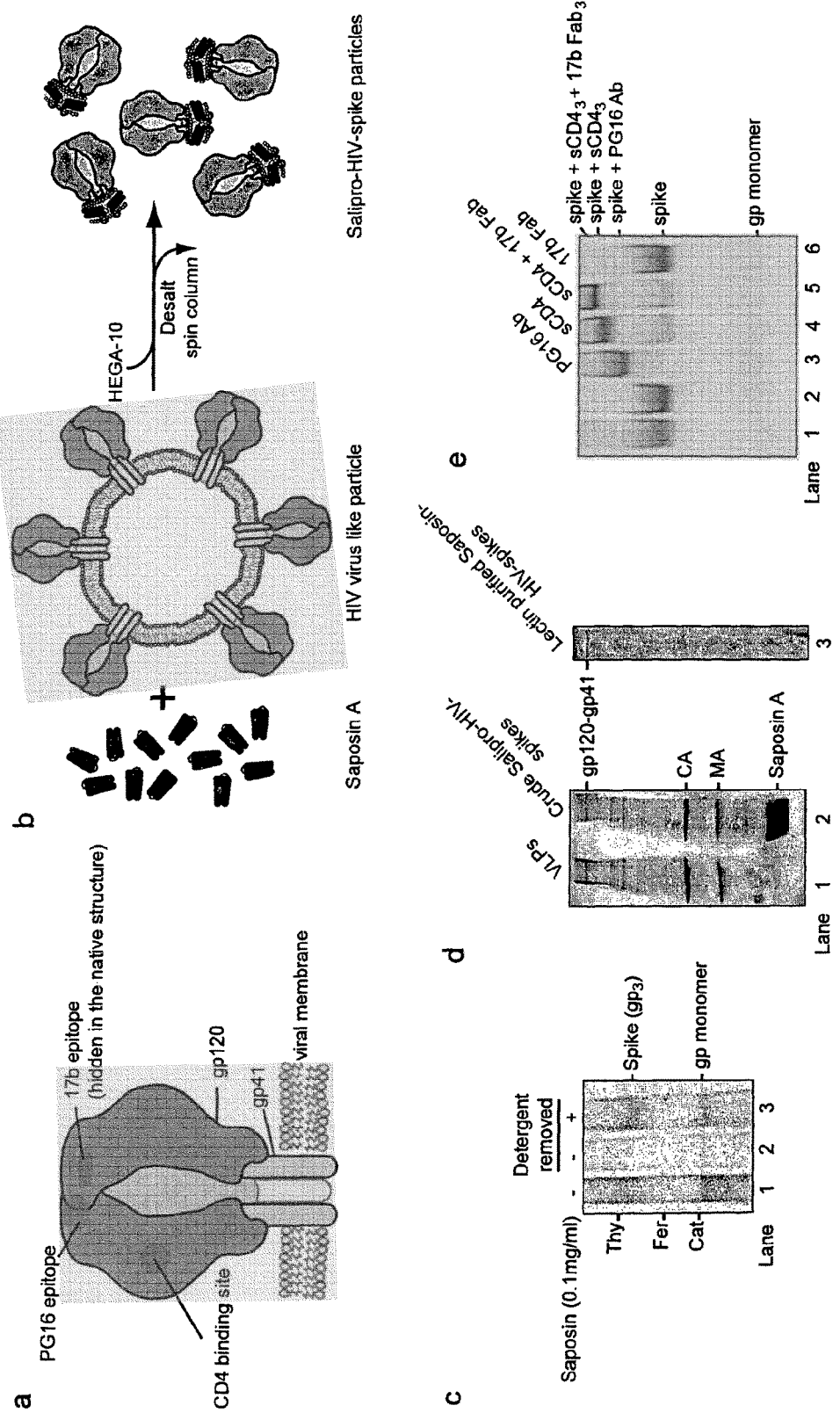
FIG. 2 is a schematic illustration of a method for reconstituting a membrane protein according to an embodiment of the invention, in particular for reconstituting spike protein particles for Salipro (Saposin A)-spike protein particle production.

FIG. 2 is a schematic illustration of a method for reconstituting a membrane protein according to an embodiment of the present invention, in particular for reconstituting spike protein particles for saposin-spike protein particle production.

FIG. 2(a) shows a schematic illustration of the HIV-1 spike protein in the viral membrane. The HIV-1 Envelope glycoprotein, i.e. the spike, consists of two subunits, the peripheral gp120 subunit (brown) and the transmembrane gp41 subunit (grey), forming a hetrotrimer. The binding site for the CD4 receptor and epitopes for the antibodies PG16 and 17b are shown (dark brown). Note that the 17b epitope is hidden in the native spike structure, but becomes exposed after CD4 receptor binding.

FIG. 2(b) shows a schematic illustration of the saposin-HIV-spike reconstitution. Purified VLPs containing HIV-1 spikes were mixed with saposin A and solubilized with HEGA-10 followed by detergent removal using a desalt spin column. The removal of the detergent allows the formation of saposin-HIV-spikes.

FIG. 2(c) illustrates the reconstitution of the HIV-1 spike protein into saposin/antigen nanoparticles. BN-PAGE analysis resolves the radioactively labelled trimeric HIV-1 spike protein (gp3) after VLP solubilisation using HEGA-10 (lane 1). A fraction of dissociated glycoprotein (gp) monomers were also observed. If HEGA-10 is removed, using a desalt column, the HIV-1 spike proteins aggregate and cannot be resolved by BN-PAGE (lane 2). Importantly, when saposin A was present during HEGA-10 removal the trimeric spike protein was resolved by the BN-PAGE, suggesting reconstitution of the HIV spike into saposin/antigen nanoparticles (lane 3). Shown is a phosphor image of the gel.

In FIG. 2(d) the purification of saposin-HIV-spike complexes is shown. Unlabelled VLPs from 14 transfected cell culture flasks (150 cm$^2$) were used for reconstituting saposin-HIV-spike particles as described. The particles were affinity purified by Galanthis Nivalis chromatograpy. Shown are non-reducing SDS-PAGE analyses of the purified VLP preparation (lane 1), the crude reconstituted saposin/antigen particle preparation (lane 2) and the lectin purified saposin/antigen preparation (lane 3). The migration of the disulfide linked gp120-gp41 complex, the capsid (CA) and the matrix (MA) proteins of the virus as well as the saposin A are indicated. The gel was stained for protein using Sypro Ruby.

FIG. 2(e) illustrates that the HIV-1 spike is stable, has a native fold and preserves its function in saposin-HIV-spike nanoparticles. Radioactively labelled and lectin purified saposin-HIV-spike particles were incubated at 37° C. for 16 h followed by 2 h incubation at 37° C. with (lanes 3-6) or without (lane 2) 10 μg/ml of the HIV-1 spike ligands, PG16 Ab (150 KDa) (lane 3), sCD4 (50 KDa) (lane 4), sCD4 and 17b Fab (50 KDa) together (lane 5) or 17b Fab alone (lane 6), and analyzed by BN-PAGE. A control sample was kept on ice without ligands (lane 1). Binding of the ligands were followed by the shift in band migration of the saposin-HIV-spike nanoparticle complexes. Note that only one PG16 Ab can bind to the trimeric spike protein due to steric reason. 17b Fab and sCD4 bind stochiometrically, adding about 150 KDa each in molecular weight to the complex, but the latter complex moves slower in the gel. Shown is a phosphor image of the gel.

FIG. 3 schematically illustrates the solubilisation of radioactively labelled HIV-1 VLP with high CMC detergents. HIV-1 VLPs were solubilised in 1×HNC buffer containing 25 mM Anameg-7 (CMC 19.5 mM) (lane 2), 9 mM HEGA-10 (CMC 7 mM) (lane 3), 14 mM C-HEGA-11 (CMC 11.5 mM) (lane 4), 9 mM MEGA-10 (CMC 6-7 mM) (lane 5), 12 mM n18 Octyl-beta-D-Thiomaltopyranoside (OT) (CMC 9 mM) (lane 6), or 10 mM Tetraethylene Glycol Monooctyl Ether (C8E4) (CMC 10 mM) (lane 7), for 10 min on ice (a) or for 30 min at 37° C. (b) and analysed by BN-PAGE. VLP solubilised in TX100 (TX) on ice was analyzed as control (lane 1). Migration of spikes and gp monomers are indicated. Note the dissociation of spikes into monomers by the 37° C. incubation.

FIG. 4 shows the optimisation of the amount of saposin A needed for efficient saposin-HIV-spike nanoparticle formation. Radioactively labelled VLPs were mixed with saposin A (230-0.77 μg/ml) followed by 10 min solubilisation on ice using 9 mM HEGA-10 in 1×HNC buffer. HEGA-10 was then removed and the amount of reconstituted saposin-HIV-spike particles was monitored by BN-PAGE. About 100 μg/ml saposin A was found to be optimal.

The saposin/antigen particles used in the invention are a nanoparticle system of a saposin-like compound, which can oligomerize at proper conditions forming a cluster of nanoparticles, instead of micelles, where an inside of the nanoparticles (of the cluster) provides a lipid membrane mimicking environment.

FIG. 6 illustrates that the HIV-1 spike is stable, has a native fold and preserves its function in saposin/antigen nanoparticles for at least 90 h at 37° C. Radioactively labelled and lectin purified saposin-HIV-spike particles were incubated at 37° C. for 90 h followed by 2 h incubation at 37° C. with (lanes 3-6) or without (lane 2) 10 μg/ml of the HIV-1 spike ligands, PG16 Ab (150 KDa) (lane 3), sCD4 (50 KDa) (lane 4), sCD4 and 17b Fab (50 KDa) together (lane 5) or 17b Fab alone (lane 6), and analyzed by BN-PAGE. A control sample was kept on ice without ligands (lane 1). Binding of the ligands were followed by the shift in band migration of the saposin-HIV-spike nanoparticle complexes, similar as figure Xd. Note the preservation of the HIV-1 spike structure in the saposin-HIV-spike particles after this extreme incubation.

In FIG. 7 a negative stain EM analysis of purified saposin-HIV-spike particles is provided. Shown is a raw EM image (left panel), and some selected particles (right panel). These are of similar size as earlier published HIV-1 spike structures.

The product of the process of the invention is present in a solution. It can be lyophilized or deep freezed.

The following examples further describe the invention.

EXAMPLE 1

Specifically, HIV-1 virus like particles (VLP) is produced by calcium phosphate-mediated DNA transfection of 293T cells. VLP released into the cell culture media are then purified by ultracentrifugation (Beckman SW55 rotor, 28,000 rpm for 17 h) in a 20-60% sucrose density step gradient. To generate saposin-spikes, the VLPs must first be solubilized by a traditional detergent and then exchanged to saposin A. This is possible to do by molecular sieving if the detergent has a high critical micelle concentration (CMC), i.e. in the mM range. Furthermore, the detergent must be mild enough to preserve the native trimeric structure of the spike during solubilization. In these experiments we use the detergent HEGA-10, with CMC at 7 mM. Accordingly, purified VLPs are lysed for 10 min on ice with 9 mM HEGA-10 in the presence of 90 µg/ml saposin A. Then HEGA-10 is removed from the sample using a Zeba desalting spin column, 7 kDa cut off (Thermo Fisher Scientific) according to the instructions in the User Manual. The column only removes the HEGA-10 detergent and not the saposin, which replaces the detergent in the spike detergent complexes. The saposin-spikes product elutes from the column in the void volume. If saposin A was omitted from the experiment, the HIV-1 spikes aggregated and could not be resolved in BN-PAGE. FIG. 2 illustrates the method that was developed for fast and efficient saposin-spike production.

The particles obtained by the method of the invention according to various embodiments are robust over concentrating using standard centrifugal filter units, freezing and thawing. Also, practical experiments revealed that the particles of the invention display a certain degree of thermo stability. In addition, it is probably possible to freeze-dry, store and re-hydrate the particles of the invention without any major quality deterioration observable. Experiments have proved that HIV-spike protein particles are stable over a period of time of over 90 hours at 37° C. with preserved structure and functionality, which proves long-term stability (FIG. 6). It has also been proved that known neutralising HIV-1 antibodies bind strongly to these spike protein particles and that even more importantly, that no neutralizing antibodies bind to the spike protein particles. This is exactly what is required for being able to produce an efficient HIV-1 vaccine. Thus, the spike protein particles are suitable for this application. They may also be suitable as development tools for vaccines.

Embodiments of the present invention are concerned with vaccines protective against HIV, in particular HIV-1 and with novel reconstituted membrane protein particles and a method for producing the same for use in such vaccines, vaccine compositions or tools for producing or assisting when producing the same, for instance kits for quick reconstitution of membrane enveloped proteins at the same time providing protein stability as well as conserved structure and functionality, but is also applicable to other viruses such as flue, Ebola and SARS The invention is suitable for large-scale production.

EXAMPLE 2

Purification of Saposin A

Purified saposin A was prepared as follows. Saposin A protein expression was carried out using a vector with the coding region for human saposin A (SEQ ID NO: 1) inserted into a pNIC-Bsa4 plasmid and transformed and expressed in E. coli Rosetta gami-2 (DE3) (Novagen) strains. Cells were grown at 37° C. in TB medium supplemented with Tetracycline, Chloramphenicol and Kanamycin and induced with 0.7 mM IPTG. Three hours after induction, the cells were collected by centrifugation at 12.000×g for 15 min. The supernatant was discarded, the cell pellet was resuspended using lysis buffer (20 mM Hepes pH 7.5, 150 mM NaCl, 20 mM Imidazol) and disrupted by sonication. Lysates were subjected to centrifugation at 26.000×g for 30 min, the supernatant heated to 85° C. for 10 min, followed by an additional centrifugation step at 26.000×g for 30 min. Preparative IMAC purification was performed by batch-adsorption of the supernatant by end-over-end rotation with Ni Sepharose™ 6 Fast Flow medium for 60 min. After binding of saposin A to the IMAC resin, the chromatography medium was packed in a 10-mm-(i.d.) open gravity flow column and unbound proteins were removed by washing with 15 bed volumes of lysis buffer. The resin was washed with 15 bed volumes of wash buffer WB2 (20 mM Hepes pH 7.5, 150 mM NaCl, 40 mM Imidazol). Saposin A was eluted by addition of five bed volumes of elution buffer EB (20 mM Hepes pH 7.5, 150 mM NaCl, 400 mM Imidazol). The eluate was dialyzed overnight against gel filtration buffer GF pH 7.5 (20 mM Hepes pH 7.5, 150 mM NaCl) supplemented with recombinant TEV protease. TEV protease containing an un-cleavable His-tag was removed from the eluate by passing it over 2 ml IMAC resin. Cleaved target proteins were concentrated to a volume of 5 ml using centrifugal filter units and loaded onto a HiLoad Superdex™ 200 16/60 GL column using an AKTAexplorer™ 10 chromatography system (both GE Healthcare). Peak fractions were pooled and concentrated to 1.2 mg/ml protein. The protein sample was flash frozen in liquid nitrogen and stored at −80 C.

The invention claimed is:

1. A reconstituted saposin-like protein (SAPLIP)-antigen nanoparticle comprising at least one hydrophobic or partially hydrophobic antigen molecule from a virus, a bacterium, fungus, protozoan, parasite, a human neoplastic cell or an animal neoplastic, tumour or cancer cell, reconstituted in a lipid membrane mimicking environment selected from a lipid binding protein such that the antigen molecule(s) is/are self-assembled therein, wherein the lipid binding protein is a saposin-like protein (SAPLIP), and wherein the antigen particle was obtained by a method comprising the steps of
    a) providing a virus, or cell comprising an antigen molecule,
    b) if a cell is provided in step a), purifying said cell comprising the antigen molecule,
    c) solubilizing the antigen molecule in a solubilizing agent that preserves intact the antigen molecule upon solubilisation,
    d) reconstituting the antigen molecule in a saposin-like protein (SAPLIP).

2. The reconstituted antigen particle according to claim 1, wherein the lipid membrane mimicking environment is a saposin-like protein, and interacts with the antigen molecules assembling them into the saposin-like protein particles.

3. The reconstituted antigen particle according to claim 2, wherein the saposin-like protein is selected from one or more of saposin A, saposin B, saposin C and saposin D.

4. The reconstituted antigen particle according to claim 1, wherein the lipid membrane mimicking environment is a saposin-like protein and wherein the antigen molecules are HIV-1 spike proteins.

5. An immunogenic composition comprising the reconstituted antigen particle of claim 1.

6. The immunogenic composition of claim 5 for prophylactic or therapeutic vaccination.

7. A method for producing a reconstituted saposin-like protein (SAPLIP)-antigen nanoparticle comprising at least one hydrophobic or partially hydrophobic antigen molecule from a virus, a bacterium, fungus, protozoan, parasite, a human neoplastic cell or an animal neoplastic, tumour or cancer cell, the method comprising the steps of
providing a virus, or cell comprising an antigen molecule, wherein, when a cell is provided, purifying the cell comprising the antigen molecule,
solubilizing the antigen molecule in a solubilizing agent that preserves intact an antigen molecule upon solubilisation,
reconstituting the antigen molecule in a lipid-binding polypeptide that provides a lipid membrane mimicking environment, wherein the lipid binding protein is a saposin-like protein (SAPLIP), wherein the solubilized antigen self-assembles into stable lipid binding polypeptide-antigen particles, wherein the reconstituted saposin-like protein (SAPLIP)-antigen nanoparticle is reconstituted in a lipid membrane mimicking environment selected from a lipid binding protein such that the at least one hydrophobic or partially hydrophobic antigen molecule(s) is/are self-assembled therein.

8. The method according to claim 7, wherein the antigen molecule is an integral membrane protein, an integral membrane protein complex, a peripheral membrane protein or a peripheral membrane protein complex.

9. The method according to claim 8, wherein the integral membrane particle is a viral spike protein, such as a trimeric envelope glycoprotein spike of HIV-1.

10. The method according to claim 7, wherein the saposin-like protein is selected from saposin A, saposin B, saposin C and/or saposin D.

11. The method according to claim 7, wherein the antigen molecule is reconstituted in a saposin-like protein without adding any additional lipids.

12. The method according to claim 7, wherein the antigen molecule is solubilized in a solubilizing agent selected from one or more of HEGA-10, C-HEGA-11 or MEGA-10.

13. A method for making a vaccine comprising a reconstituted saposin-like protein (SAPLIP)-antigen nanoparticle, the method comprising:

A) preparing a reconstituted saposin-like protein (SAPLIP)-antigen nanoparticle comprising the steps:
  a) providing at least one hydrophobic or partially hydrophobic antigen molecule from a virus, a bacterium, a fungus, a protozoan, a parasite, a human neoplastic cell, an animal neoplastic cell, a tumour or a cancer cell,
  b) if a cell is provided in step a), purifying said cell comprising the antigen molecule,
  c) solubilizing the antigen molecule in a solubilizing agent that preserves intact the antigen molecule upon solubilisation, and
  d) reconstituting the antigen molecule in a saposin-like protein (SAPLIP), and
B) formulating the reconstituted saposin-like protein (SAPLIP)-antigen nanoparticle for vaccine administration, wherein the at least one antigen molecule is/are self-assembled in the nanoparticle.

14. A reconstituted saposin-like protein (SAPLIP)-antigen nanoparticle comprising at least one integral membrane or peripheral membrane protein from a eukaryotic cell as an antigen molecule reconstituted in a lipid membrane mimicking environment selected from a lipid binding protein such that the antigen molecule(s) is/are self-assembled therein, wherein the lipid binding protein is a saposin-like protein (SAPLIP), and wherein the antigen particle was obtained by a method comprising the steps of
  a) providing a cell comprising the antigen molecule,
  b) purifying said cell comprising the antigen molecule,
  c) solubilizing the antigen molecule in a solubilizing agent that preserves intact the antigen molecule upon solubilisation,
  d) reconstituting the antigen molecule in a saposin-like protein (SAPLIP).

15. A method for producing a reconstituted saposin-like protein (SAPLIP)-antigen nanoparticle comprising at least one integral membrane or peripheral membrane protein from a eukaryotic cell as an antigen molecule, the method comprising the steps of:
providing a cell comprising the antigen molecule and purifying the cell comprising the antigen molecule,
solubilizing the antigen molecule in a solubilizing agent that preserves intact the antigen molecule upon solubilisation,
reconstituting the antigen molecule in a lipid-binding polypeptide that provides a lipid membrane mimicking environment,
wherein the lipid binding protein is a saposin-like protein (SAPLIP), wherein the solubilized antigen self-assembles into stable lipid binding polypeptide-antigen particles, wherein the reconstituted saposin-like protein (SAPLIP)-antigen nanoparticle is reconstituted in a lipid membrane mimicking environment selected from a lipid binding protein such that the at least one integral membrane or peripheral membrane protein from a eukaryotic cell is/are self-assembled therein.

* * * * *